(12) United States Patent
Iida et al.

(10) Patent No.: US 6,893,658 B1
(45) Date of Patent: May 17, 2005

(54) SOFT CAPSULES

(75) Inventors: Yoshimitsu Iida, Tokyo (JP); Yutaka Ogawa, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 17 days.

(21) Appl. No.: 10/069,755

(22) PCT Filed: Aug. 31, 2000

(86) PCT No.: PCT/JP00/05922

§ 371 (c)(1),
(2), (4) Date: Feb. 28, 2002

(87) PCT Pub. No.: WO01/15702

PCT Pub. Date: Mar. 8, 2001

(30) Foreign Application Priority Data

Aug. 31, 1999 (JP) .......................................... 11/244828

(51) Int. Cl.⁷ ................................................ A61K 9/48
(52) U.S. Cl. ...................... 424/456; 424/646; 424/648; 514/972; 514/962
(58) Field of Search ................................ 424/451, 646, 424/648; 514/972

(56) References Cited

U.S. PATENT DOCUMENTS

| 3,784,684 A | 1/1974 | Bossert et al. |
| 4,268,265 A | 5/1981 | Von Wattenwyl |
| 4,693,892 A | * 9/1987 | Hegasy et al. |
| 4,851,394 A | * 7/1989 | Kubodera |
| 5,292,727 A | 3/1994 | Godtfredsen |

FOREIGN PATENT DOCUMENTS

| JP | 52-151724 | * 12/1977 |
| JP | 55-141242 | * 11/1980 |
| JP | 63-166824 | * 2/1988 |
| JP | 1-152911 | * 6/1989 |

OTHER PUBLICATIONS

XP–002205586 (Abstract for J03264532), Teijin Ltd, "Activated Vitamin–D Comprises (e.g. Alpha–Hydroxy Vitamin–D Useful for Treatment of Alveolar Bone Atrophy)", Nov. 25, 1991.

XP–002205585 (Abstract for J04046122), Nihon Iyakuhin Kogyo KK, "Novel Stable Formulation Containing Activated Vitamin–D3 Compounds—Contains Middle Chain Fatty Acid Tri Glyceride Solution or Suspension of Activated Compounds in Hard Capsule with Band Seal", Feb. 17, 1992.

XP–002205587 (Abstract for J08012580), Chugai Pharm Co Ltd, "Pharmaceutical for Stimulation of Bone Fusion—Shortens Treatment Period and Prevents Refracture", Jan. 16, 1996.

XP–002205584 (Abstract for J63215641), Toyo Jozo KK, "Gelatin Coating Membrane Composition—Containing Caramel and an Amino Acid Compound", Sep. 8, 1988.

XP–002205588 (Abstract for J11035469), Teijin Ltd, "Preventive and Treatment Agent for Chronic Cardiac Failure—Contains (e.g., Active Vitamin–D Derivatives, Particularly e.g., 1–alpha, 25–dihydroxy VD3)", Feb. 9, 1999.

* cited by examiner

*Primary Examiner*—Edward J. Webman
(74) *Attorney, Agent, or Firm*—Browdy and Neimark, P.L.L.C.

(57) ABSTRACT

An object of the present invention is to provide soft capsule formulations of active vitamins D, well-suited to practical production with easy discrimination of active ingredient levels, in which stability of the active vitamins $D_3$ to light and heat is ensured, and which material is highly safe to the human body. According to the present invention, soft capsule formulations of active vitamins $D_3$ can be obtained-wherein the capsule shell contains a white pigment and yellow iron oxide and/or red iron oxide, or titanium oxide and caramel, or yellow iron oxide.

14 Claims, No Drawings

SOFT CAPSULES

TECHNICAL FIELD

The present invention relates to soft capsule formulations containing active vitamins $D_3$.

BACKGROUND ART

Active vitamins $D_3$ such as 1α-hydroxycholecalciferol (1α-hydroxyvitamin $D_3$) and 1α,25-dihydroxycholecalciferol (1α,25-dihydroxyvitamin $D_3$) have the effects of promoting calcium absorption in the small intestine, controlling bone metabolism in the bone, controlling parathyroid hormone production in the parathyroid, inducing differentiation in tumor cells, suppressing immune response, etc. Therefore, they are considered to be effective for treating renal failure associated with lowered calcium absorption, osteoporosis caused by abnormal bone metabolism, hyperparathyroidism, malignant tumors, autoimmune diseases and the like.

However, all these compounds are unstable to light and heat and to be put to use in medical applications, this problem is required to be overcome. Formulations containing active vitamins $D_3$ as active ingredients are used at varying active ingredient levels because the dose varies with the disease or condition. Thus, it is important that the active ingredient level in each formulation can be readily discriminated in order to prevent medical fault.

It is also important to ensure content uniformity of active vitamins $D_3$ in formulations because they are effective at a very low dose such as several tens of micrograms.

Known formulations of active vitamins $D_3$ include a soft capsule formulation of an active vitamin $D_3$ wherein an oily solution of the active vitamin $D_3$ is encapsulated with a capsule shell containing 1.0% by weight or less of a UV absorber having a light transmittance of 10% or less at a wavelength of 310 mμ in 0.01% by weight aqueous solutions and having absorption in the visible range (JPA No. 84023/1979). Other soft capsule formulations for stabilizing light-unstable compounds so far reported include a soft capsule formulation wherein a dye absorbing a specific wavelength of light and an opacifier are homogeneously dispersed in a gelatin shell (JPA No. 28621/1973); a soft capsule formulation wherein Food Color Yellow No. 5 is homogeneously dispersed in a soft capsule shell to stabilize light-unstable compounds in said soft capsule shell (JPA No. 22645/1980); a soft capsule formulation wherein an edible tar-based dye such as Food color Yellow No. 4 is dispersed in a capsule shell (JPA No. 13511/1983), etc. However, recent scientific research has shown that a UV absorber having absorption in the visible range, and dyes used in these disclosed techniques, which are tar-based synthetic dyes or synthetic colorants, have doubtful safety. Moreover, these formulations are inconvenient for international distribution because the permitted classes of dyes vary between countries.

On the other hand, a method for stabilizing active vitamins $D_3$ without using a tar-based synthetic dye or a synthetic colorant is known, such as a soft capsule formulation using a capsule shell containing a natural dye such as cocoa dye, apigenin, carminic acid, carminic acid lake, laccaic acid or shikonin (JPA No. 53923/1987). However, it is difficult to always maintain a uniform color tone with these natural dyes, which vary in color tone with the batch lot, and also tend to be unstable.

A method for stabilizing active vitamins $D_3$ by using an inorganic compound is also known, such as a soft capsule formulation using a capsule shell containing fine particles of titanium oxide wherein at least 85% of titanium oxide has a particle diameter of 0.1 μm or less (JPA No. 166824/1988). However, titanium oxide has a white color tone, which is insufficient for discriminating active ingredient levels and requires some additional colorants to enable better discrimination.

Known colorants other than the above tar-based dyes, synthetic colorants and natural dyes include iron oxide, caramel and the like. A soft capsule formulation using iron oxide is described in JPA No. 84023/1979, which discloses a soft capsule formulation of an active vitamin $D_3$ encapsulated with a shell containing yellow iron oxide and red iron oxide, but it is reported to be insufficient in stability to heat. A method for preventing destabilization of active ingredients due to direct contact of the active ingredients with red iron oxide (diiron trioxide) in soft capsule shells is reported by JPA No. 157911/1989, which discloses a light-screening capsule formulation wherein microencapsulated red iron oxide is dispersed in a shell to prevent direct contact of red iron oxide with the drug in the capsule, but this method is not a practical means of production since it requires complex operations such as the preparation of microcapsules containing red iron oxide. A gelatin shell colored with caramel (JPA No. 127448/1980) is also known, but its effect on the stability of active vitamins $D_3$ to light or heat is unknown.

DISCLOSURE OF THE INVENTION

The present invention provides soft capsule formulations of active vitamins $D_3$ well-suited to practical production with easy discrimination of active ingredient levels, in which stability of the active vitamins $D_3$ to light and heat is ensured by using a material which is highly safe to the human body.

As a result of careful studies, the inventors accomplished the present invention on the basis of the finding that soft capsule formulations of active vitamins $D_3$ with excellent stability to light and heat and good discrimination that can be prepared by a process well-suited to practical production can be obtained by using a capsule shell containing a white pigment and yellow iron oxide and/or red iron oxide, or a white pigment and caramel.

Accordingly, the present invention provides a soft capsule formulation comprising: an oily solution of an active vitamin $D_3$; and a soft capsule shell which contains a white pigment and yellow iron oxide and/or red iron oxide and encapsulates the oily solution of an active vitamin $D_3$.

The present invention also provides a soft capsule formulation comprising: an oily solution of an active vitamin $D_3$; and a soft capsule shell which contains a white pigment and caramel and encapsulates the oily solution of active vitamin $D_3$.

PREFERRED EMBODIMENTS OF THE INVENTION

The present application claims priority based on Japanese Patent Application No. 244828/1999, the disclosure of which is wholly incorporated herein as a reference.

Active vitamins $D_3$ used in the present invention include, for example, 1α-hydroxyvitamin $D_3$, 24-hydroxyvitamin $D_3$, 25-hydroxyvitamin $D_3$, 1α,24-dihydroxyvitamin $D_3$, 1α,25-dihydroxyvitamin $D_3$, 1α,24,25-trihydroxyvitamin $D_3$, 22-oxa-1α,25-dihydroxyvitamin $D_3$ and 2β-(3-hydroxypropyloxy)-1α,25-dihydroxyvitamin $D_3$, preferably 1α-hydroxyvitamin $D_3$ and 2β-(3-hydroxypropyloxy)-1α, 25-dihydroxyvitamin $D_3$.

Examples of the white pigments used in the present invention include titanium oxide, calcium carbonate and alumina, preferably titanium oxide and calcium carbonate, more preferably titanium oxide.

Examples of the titanium oxide used in the present invention includes titanium dioxide ($TiO_2$) of anatase and rutile types, both of which are commercially available, with the anatase type being preferred. The particle diameter of the titanium oxide is not particularly limited, however those having an average particle diameter of 0.2–0.5 μm are used in general; those having smaller particle diameters can be also employed. Such titanium oxide treated to improve resistance to discoloration as described in JPA No. 222442/1999 may also be used. The content of the titanium oxide used is preferably 98.5% by weight or more expressed as dry content.

The amount of white pigment used is preferably 0.1% by weight or more, particularly 0.5% by weight or more, of the total amount of capsule shell components. It is preferably 1.5% by weight or less, particularly 1.0% by weight or less, of the total amount of capsule shell components.

As used herein, the total amount of capsule shell components means the amount of the materials of capsule shell excluding water.

Yellow iron oxide used in the present invention is $Fe_2O_3$ ($H_2O$), also called yellow diiron trioxide. Commercially available yellow iron oxide can be conveniently used, but the content of diiron trioxide in the ignition product is preferably 98.0% or more.

Red iron oxide used in the present invention is $Fe_2O_3$, also called diiron trioxide or red oxide. Commercial products can be conveniently used, but the content of diiron trioxide in the ignition product is preferably 98.0% or more.

If the capsule shell components include a white pigment and yellow iron oxide and/or red iron oxide, the amount of white pigment and yellow iron oxide and/or red iron oxide contained in the capsule shell depends on the light screening properties, heat resistance and desired color tone of the capsule shell but the total amount of white pigment, yellow iron oxide and red iron oxide is preferably 0.11% by weight or more, more preferably 0.51% by weight or more of the total amount of capsule shell components. It is preferably 1.51% by weight or less, more preferably 1.1% by weigh or less of the total amount of capsule shell components. The total amount of yellow iron oxide and red iron oxide contained in the capsule shell may be preferably 0.01% or more and 1.0% by weight or less. Here, either one or both of yellow iron oxide and red iron oxide can be used.

In order to control color tone, a dye such as caramel can further be added.

Caramel used in the present invention is obtained by heat-treating an edible carbohydrate such as D-glucose, sucrose, invertose, millet jerry, starch hydrolyzate, molasses, etc. The molecular weight of caramel is not particularly limited, but a caramel product free from components having a molecular weight below a certain value as described in JPA No. 127448/1980 may be used.

If caramel is contained in the capsule shell in the present invention, the amount of caramel contained in the capsule shell depends on the desired color tone and strength of the capsule shell, but preferably ranges from 0.05 to 1.5% by weight of the total amount of capsule shell components. If caramel is contained in the capsule shell, a white pigment is preferably also contained in the capsule shell. The total amount of white pigment and caramel contained in the capsule shell depends on the desired color tone and strength of the capsule shell, but it is preferably 0.15% by weight or more and 1.55% or less of the total amount of capsule shell components. If capsule shell components include a white pigment and caramel, yellow iron oxide and/or red iron oxide may further be contained as capsule shell components, and in this case, the total amount of the white pigment, caramel, yellow iron oxide and red iron oxide is preferably 1.56% or less of the total amount of capsule shell components.

Other components of soft capsule shells may be those capable of forming a soft capsule shell with a white pigment and yellow iron oxide and/or red iron oxide or with a white pigment and caramel or the like, such as various gelatins and various plasticizers in combination with various additives. Examples of the various gelatins include gelatins derived from animals such as cattle and swine. As used herein, various gelatins include alkali-treated gelatins, acid-treated gelatins, chemically modified gelatins or the like, which may be used alone or in admixture.

Alkali-treated gelatins mean those obtained by hydrolyzing a raw material of gelatin such as collagen or ossein with an alkaline material such as a lime solution, and extracting the hydrolyzate; while acid-treated gelatins are those obtained by hydrolyzing a collagen with an acidic material such as dilute hydrochloric acid or dilute sulfuric acid. Chemically modified gelatins generally mean, but are not limited to, those prepared by reacting the amino group of a gelatin with an acid such as succinic acid, phthalic acid or acetic acid. Either the alkali-treated gelatins or the acid-treated gelatins may be used for preparing the chemically modified gelatins.

Examples of the various plasticizers include glycerin, sorbitol, maltose, glucose, maltitose, sucrose, xylitol, mannitol, erythritol, polyethylene glycols (molecular weight 400–6000), etc.

Examples of the various additives include ethyl paraoxybenzoate, propyl paraoxybenzoate, potassium sorbate, etc.

The thickness of the capsule shells may be appropriately chosen in as far as the soft capsule formulations maintain sufficient strength and disintegrate at an appropriate timing to release active vitamins $D_3$ when they are administered; the thickness is preferably 200 μm to 600 μm.

Preferably, the white pigment, yellow iron oxide and red iron oxide are homogeneously dispersed in a capsule shell. They can be dispersed by adding a mixed suspension of the white pigment and yellow iron oxide and/or red iron oxide or a mixed solution of the white pigment and caramel to a gelatin solution or adding and dispersing the white pigment into a gelatin solution and then adding yellow iron oxide and/or red iron oxide or caramel. The order of addition is not specifically limited. These white pigment, yellow iron oxide, red iron oxide and caramel can be homogeneously dispersed in a gelatin solution by using a conventional stirring or dispersing method and apparatus.

Suitable bases for the oily solutions may be those capable of forming a soft capsule formulation without impairing stability of active vitamins $D_3$, such as glycerides of fatty acids, propylene glycol fatty acid diesters, triacetin, polyethylene glycols, vegetable oils, etc., preferably glycerides of fatty acids, particularly preferably middle chain fatty acid triglycerides. These oily bases may be used alone or as a mixture of two or more. As used herein, the middle chain fatty acid triglycerides mean those based on a fatty acid triglyceride in which the fatty acid has a carbon chain length of 8–10. Examples of the vegetable oils include olive oil, soybean oil, rapeseed oil, castor oil, etc., which may be used alone or as a mixture of two or more.

The soft capsule formulations of the present invention can be prepared, for example, by encapsulating an oily solution of an active vitamin $D_3$ described above in a soft capsule shell described above using a rotary or dropping-type continuous soft capsule machine.

EXAMPLES

The following examples further illustrate the present invention without, however, limiting the invention thereto.

Example 1

To a solution of 1α-hydroxyvitamin $D_3$ dissolved at a concentration of 1.44 mg/ml in absolute ethanol was added a middle chain fatty acid triglyceride (The Nisshin Oil Mills Ltd.) to give an oily solution of 1α-hydroxyvitamin $D_3$ at a concentration of 4.8 μg/ml. Separately, a gelatin solution was prepared containing 38 parts by weight of gelatin (Nitta Gelatin Inc.), 11 parts by weight of glycerin (Kashima Chemical Co., Ltd.), 0.15 parts by weight of potassium sorbate and 50 parts by weight of purified water as well as titanium oxide (A-100, Ishihara Sangyo Kaisha, Ltd.), yellow iron oxide (Kishi Kasei Co., Ltd.) and red iron oxide (Kishi Kasei Co., Ltd.) in the amounts shown in Table 1 below. The oily 1α-hydroxyvitamin $D_3$ solution was encapsulated with the above gelatin solution containing titanium oxide, yellow iron oxide and/or red iron oxide using a continuous soft capsule machine (SPHEREX, Freund Industrial Co., Ltd.) and dried in a tumbler dryer to prepare soft capsules.

The resulting soft capsules had an average weight of 101 mg per capsule and an average solution content of 61 mg. These capsules had good color tone and discrimination from capsules obtained in other examples as evaluated by organoleptic tests (visual tests).

Comparative Example 1

Soft capsules were prepared in the same manner as in Example 1 above except that the gelatin solution contained none of titanium oxide, yellow iron oxide and red iron oxide.

The resulting soft capsules had an average weight of 100 mg per capsule and an average solution content of 60 mg.

Comparative Example 2

Soft capsules were prepared in the same manner as in Example 1 above except that the gelatin solution contained titanium oxide in the amount shown in Table 1 below instead of titanium oxide, yellow iron oxide and red iron oxide.

The resulting soft capsules had an average weight of 101 mg per capsule and an average solution content of 63 mg.

Example 2

Soft capsules were prepared in the same manner as in Example 1 above except that instead of titanium oxide, yellow iron oxide and red iron oxide, the gelatin solution contained titanium oxide and yellow iron oxide in the amounts shown in Table 1 below.

The resulting soft capsules had an average weight of 106 mg per capsule and an average solution content of 64 mg. These capsules had good color tone and discrimination as evaluated in the same manner as in Example 1.

Example 3

Soft capsules were prepared in the same manner as in Example 1 above except that instead of titanium oxide, yellow iron oxide and red iron oxide, the gelatin solution contained titanium oxide and yellow iron oxide in the amounts shown in Table 1 below.

The resulting soft capsules had an average weight of 100 mg per capsule and an average solution content of 60 mg. These capsules had good color tone and discrimination as evaluated in the same manner as in Example 1.

Example 4

Soft capsules were prepared in the same manner as in Example 1 above except that instead of titanium oxide, yellow iron oxide and red iron oxide, the gelatin solution contained titanium oxide and caramel in the amounts shown in Table 1 below.

The resulting soft capsules had an average weight of 103 mg per capsule and an average solution content of 63 mg. These capsules had good color tone and discrimination as evaluated in the same manner as in Example 1.

Example 5

Soft capsules were prepared in the same manner as in Example 1 above except that instead of titanium oxide, yellow iron oxide and red iron oxide, the gelatin solution contained titanium oxide and caramel in the amounts shown in Table 1 below.

The resulting soft capsules had an average weight of 100 mg per capsule and an average solution content of 61 mg. These capsules had good color tone and discrimination as evaluated in the same manner as in Example 1.

TABLE 1

Charges of titanium oxide, yellow iron oxide and red iron oxide

| Soft capsule | Titanium oxide | Yellow iron oxide | Red iron oxide | Caramel |
|---|---|---|---|---|
| Example 1 | 0.80 | 0.09 | 0.01 | — |
| Example 2 | 0.85 | 0.05 | — | — |
| Example 3 | 0.60 | 0.30 | — | — |
| Example 4 | 0.50 | — | — | 1.00 |
| Example 5 | 1.00 | — | — | 0.10 |
| Comparative example 1 | — | — | — | — |
| Comparative example 2 | 1.00 | — | — | — |

In Table 1 above, each value represents the charge (expressed in % by weight) of each component relative to the total amount of the materials of the shell (excluding water). "-" means that the component is not added.

Example 6

To a solution of 2β-(3-hydroxypropyloxy)-1α,25-dihydroxyvitamin $D_3$ dissolved at a concentration of 0.488 mg/ml in absolute ethanol was added a middle chain fatty acid triglyceride (The Nisshin Oil Mills Ltd.) to give an oily solution of 2β-(3-hydroxypropyloxy)-1α,25-dihydroxyvitamin $D_3$ at a concentration of 8.0 μg/ml. Separately, a gelatin solution was prepared containing 38 parts by weight of gelatin (Nitta Gelatin Inc.), 11 parts by weight of glycerin (Kashima Chemical Co., Ltd.) and 50 parts by weight of purified water as well as titanium oxide (A-100, Ishihara Sangyo Kaisha, Ltd.) and red iron oxide (Kishi Kasei Co., Ltd.) in the amounts shown in Table 2 below. The oily 2β-(3-hydroxypropyloxy)-1α,25-dihydroxyvitamin $D_3$ solution was encapsulated with the above gelatin solution containing titanium oxide and red iron oxide using the continuous soft capsule machine to prepare soft capsules.

The resulting soft capsules had an average weight of 100 mg per capsule and an average solution content of 60 mg. These capsules had good color tone and discrimination as evaluated in the same manner as in Example 1.

Comparative Example 3

Soft capsules were prepared in the same manner as in Example 6 above except that the gelatin solution contained neither titanium oxide nor red iron oxide.

The resulting soft capsules had an average weight of 100 mg per capsule and an average solution content of 60 mg.

Comparative Example 4

Soft capsules were prepared in the same manner as in Example 6 above except that the gelatin solution contained titanium oxide in the amount shown in Table 2 below in addition to 35 parts by weight of gelatin, 12 parts by weight of glycerin and 53 parts by weight of purified water.

The resulting soft capsules had an average weight of 170 mg per capsule and an average solution content of 100 mg.

TABLE 2

Charges of titanium oxide, yellow iron oxide and red iron oxide

| Soft capsule | Titanium oxide | Yellow iron oxide | Red iron oxide | Caramel |
|---|---|---|---|---|
| Example 6 | 0.6 | — | 0.3 | — |
| Comparative example 3 | — | — | — | — |
| Comparative example 4 | 1.00 | — | — | — |

In Table 2 above, each value represents the charge (expressed in % by weight) of each component relative to the total amount of the materials of the shell (excluding water). "-" means that the component is not added.

Test Example 1: Accelerated Light Stability Testing 1

Soft capsules prepared in Examples 1–5 and Comparative examples 1 and 2 above were left for 171 hours under fluorescent lighting at 3500 lux (integrated illumination 600,000 lux.hr) and then measured for the residual level of 1α-hydroxyvitamin $D_3$ by high performance liquid chromatography under the measurement conditions below. Color tone stability was also evaluated by visually comparing the color tone of soft capsules after irradiation to the color tone of non-irradiated soft capsules.

Measurement conditions for the residual level:

Apparatus: a high performance liquid chromatography made by Shimadzu Corporation (autoinjector SIL-10A, solvent delivery unit LC-10AD, system controller SCL-10A, detector SPD-10A, column oven CTO-10A/10AC, chromatopack C-R7Apuls)

Column: Waters Symmetry C18 3.5 μm 4.6×150 mm

Sample volume: 200 μL (sample concentration: about 125 ng/ml)

Column temperature: 25° C.

Mobile phase: acetonitrile:water:tetrahydrofuran:acetic acid=1350:400:250:1 (v/v)

Flow rate: 1 ml/min

Detector: UV detector at 265 nm.

The measurement results are shown in Table 3. These results showed that soft capsules of the present invention have excellent light stability. Soft capsules of the present invention were also found to have excellent stability in color tone under irradiation.

TABLE 3

Residual level of 1α-hydroxyvitamin $D_3$ in accelerated light stability testing

| Soft capsule | Residual level (%) |
|---|---|
| Example 1 | 95.2 |
| Example 2 | 98.1 |
| Example 3 | 99.1 |
| Example 4 | 95.5 |
| Example 5 | 97 4 |
| Comparative example 1 | 52.4 |
| Comparative example 2 | 96.2 |

Test Example 2: Accelerated Light Stability Testing 2

Soft capsules prepared in Example 6 and Comparative examples 3 and 4 above were left for 200 hours under fluorescent lighting at 3000 lux (integrated illumination 600,000 lux.hr) and then measured for the residual level of 2β-(3-hydroxypropyloxy)-1α,25-dihydroxyvitamin $D_3$ by high performance liquid chromatography under the measurement conditions below. Color tone stability was also evaluated by visually comparing the color tone of soft capsules after irradiation to the color tone of non-irradiated soft capsules.

Measurement conditions for the residual level:

Apparatus: a high performance liquid chromatography made by Shimadzu Corporation (autoinjector SIL-10A, solvent delivery unit LC-10AD, system controller SCL-10A, detector SPD-10A, column oven CTO-10AC)

Analyzer: Waters Millennium 32

Column: YMC A-004 SIL 5 um 4.6×300 mm

Sample volume: 50 μL (sample concentration: about 5 ng/ml)

Column temperature: 25° C.

Mobile phase: dichloromethane:methanol:acetic acid:water=1000:15:13:3.5 (v/v)

Flow rate: 1.8 ml/min

Detector: UV detector at 265 nm.

The measurement results are shown in Table 4. These results showed that soft capsules of the present invention have excellent light stability. Soft capsules of the present invention were also found to have excellent stability in color tone under irradiation.

TABLE 4

Residual level of 2β-(3-hydroxypropyloxy)-1α,25-
dihydroxyvitamin $D_3$ in accelerated light stability testing

| Soft capsule | Residual level (%) |
| --- | --- |
| Example 6 | 97.5 |
| Comparative example 3 | 1.4 |
| Comparative example 4 | 95.1 |

Test Example 3: Accelerated Heat Stability Testing

Soft capsules prepared in Examples 1–5 and Comparative examples 1 and 2 above were stored at 50° C. for 1 month and then measured for the residual level of 1α-hydroxyvitamin $D_3$ by high performance liquid chromatography under the same measurement conditions as in Test example 1 above. The measurement results are shown in Table 5. These results showed that soft capsules of the present invention have sufficient thermal stability.

TABLE 5

Residual level of 1α-hydroxyvitamin $D_3$ in
accelerated heat stability testing

| Soft capsule | Residual level (%) |
| --- | --- |
| Example 1 | 90.9 |
| Example 2 | 85.5 |
| Example 3 | 89.0 |
| Example 4 | 90.0 |
| Example 5 | 85.3 |
| Comparative example 1 | 91.5 |
| Comparative example 2 | 87.6 |

INDUSTRIAL APPLICABILITY

Soft capsule formulations of the present invention are useful as soft capsule formulations of active vitamins $d_3$ because they have great advantages such as (i) excellent stability to light and heat, (ii) good discrimination with controllable color tone, (iii) excellent safety due to the use of a white pigment, yellow iron oxide, red iron oxide and caramel widely known as safe to human, (iv) excellent stability in color tone, (v) suitability for practical production, etc.

What is claimed is:

1. A soft capsule formulation comprising:
an oily solution of an active vitamin $D_3$; and
a soft capsule shell of 200 μm to 600 μm thickness consisting of gelatin, 0.1 to 1.5% by weight of titanium oxide and 0.01 to 1.0% by weight of yellow iron oxide and/or red iron oxide based on the total weight of said soft capsule shell, optionally a dye, optionally another white pigment, optionally a plasticizer, and optionally one or more of ethyl-paraoxybenzoate, propylparaoxybenzoate and potassium sorbate, and
encapsulates said oily solution of an active vitamin $D_3$.

2. A soft capsule formulation according to claim 1 wherein said dye is present and comprises 0.05 to 1.5% by weight of caramel based on the total weight of said soft capsule shell.

3. The soft capsule formulation of claim 1 wherein said oily solution comprises at least one base material selected from the group consisting of fatty acid glycerides, propylene glycol fatty acid diesters, triacetin, polyethylene glycols and vegetable oils.

4. The soft capsule formulation of claim 3, wherein the base of the oily solution comprises a fatty acid glyceride.

5. The soft capsule formulation of claim 1 wherein the active vitamin $D_3$ is selected from 1α-hydroxyvitamin $D_3$, 24-hydroxyvitamin $D_3$, 25-hydroxyvitamin $D_3$, 1α,24-dihydroxyvitamin $D_3$, 1α,25-dihydroxyvitamin $D_3$, 1α,24,25-trihydroxyvitamin $D_3$, 22-oxa-1α,25-dihydroxyvitamin $D_2$ and 2β-(3-hydroxypropyloxy)-1α,25-dihydroxyvitamin $D_3$.

6. The soft capsule formulation of claim 2 wherein said oily solution comprises at least one base material selected from the group consisting of fatty acid glycerides, propylene glycol fatty acid diesters, triacetin, polyethylene glycols and vegetable oils.

7. The soft capsule formulation of claim 6, wherein the base material for the oily solution comprises a fatty acid glyceride.

8. The soft capsule formulation of claim 2 wherein the active vitamin $D_3$ is selected from 1α-hydroxyvitamin $D_3$, 24-hydroxyvitamin D, 25-hydroxyvitamin $D_3$, 1α,24-dihydroxyvitamin $D_3$, 1α,25-dihydroxyvitamin $D_2$, 1α,24,25-trihydroxyvitamin $D_3$, 22-oxa-1α, 25-dihydroxyvitamin $D_3$ and 2β-(3-hydroxypropyloxy)-1α, 25-dihydroxyvitamin $D_3$.

9. A soft capsule formulation comprising;
an oily solution of an active vitamin $D_3$; and
a soft capsule shell of 200 μm to 600 μm thickness consisting essentially of gelatin, 0.1 to 1.5% by weight of a white pigment and 0.01 to 1.0% by weight yellow iron oxide and/or red iron oxide based on the total weight of said soft capsule shell, and encapsulates said oily solution of an active vitamin $D_3$;
wherein said white pigment and said iron oxide within said soft capsule shell constitute a homogeneous mixture.

10. The soft capsule formulation of claim 9 wherein said soft capsule shell further comprises 0.05 to 1.5% by weight of caramel.

11. The capsule formulation of claim 9 or 10 wherein the white pigment is titanium oxide.

12. The soft capsule formulation of claim 9 wherein said oily solution comprises at least one base material selected from the group consisting of fatty acid glycerides, propylene glycol fatty acid diesters, triacetin, polyethylene glycols and vegetable oils.

13. The soft capsule formulation of claim 12 wherein the base for the oily solution comprises a fatty acid glyceride.

14. The soft capsule formulation of claim 9 wherein the active vitamin $D_3$ is selected from 1α-hydroxyvitamin $D_3$, 24-hydroxyvitamin $D_3$, 25-hydroxyvitamin $D_3$, 1α,24-dihydroxyvitamin $D_3$, 1α,25-dihydroxyvitamin $D_3$, 1α,24,25-trihydroxyvitamin $D_3$, 22-oxa-1α,25-dihydroxyvitamin $D_2$ and 2β-(3-hydroxypropyloxy)-1α,25-dihydroxyvitamin $D_3$.

* * * * *